United States Patent [19]

Ardecky et al.

[11] Patent Number: 5,310,929
[45] Date of Patent: May 10, 1994

[54] PRODRUGS OF IMIDAZOLE CARBOXYLIC ACIDS AS ANGIOTENSIN II RECEPTOR ANTAGONISTS

[75] Inventors: Robert J. Ardecky, Encinitas, Calif.; Carol L. Ensinger, Newark, Del.; James R. Pruitt, Landenberg, Pa.

[73] Assignee: E. I. Du Pont de Nemours and Company, Wilmington, Del.

[21] Appl. No.: 926,795

[22] Filed: Aug. 6, 1992

[51] Int. Cl.$^5$ ............... C07D 403/14; C07D 403/12; C07D 401/14; A61K 31/41; A61K 31/415
[52] U.S. Cl. ................... 548/253; 546/210; 548/314.7; 548/335.51
[58] Field of Search ............ 548/253, 314.7, 334.5; 514/381, 396, 397, 341, 339; 546/210

[56] References Cited

U.S. PATENT DOCUMENTS

| 5,137,902 | 8/1992 | Carini | 548/253 |
| 5,138,069 | 8/1992 | Carini et al. | 548/253 |

FOREIGN PATENT DOCUMENTS

| 0459136A1 | 4/1991 | European Pat. Off. |
| 0434249A2 | 11/1992 | European Pat. Off. |
| WO89/06233 | 1/1989 | PCT Int'l Appl. |
| WO91/00277 | 6/1990 | PCT Int'l Appl. |
| WO91/00281 | 6/1990 | PCT Int'l Appl. |
| WO92/00977 | 7/1991 | PCT Int'l Appl. |

*Primary Examiner*—David B. Springer

[57] ABSTRACT

Prodrugs of imidazole carboxylic acids which are AII antagonists useful in treating hypertension, pharmaceutical compositions thereof and a method of treating hypertension using such prodrugs are disclosed.

10 Claims, No Drawings

PRODRUGS OF IMIDAZOLE CARBOXYLIC ACIDS AS ANGIOTENSIN II RECEPTOR ANTAGONISTS

FIELD OF THE INVENTION

This invention relates to substituted imidazoles useful as angiotensin II (AII) blockers, and more particularly, to prodrugs of imidazole carboxylic acids which are AII antagonists useful in treating hypertension or congestive heart failure.

BACKGROUND OF THE INVENTION

Compounds which inhibit the action of the hormone angiotensin II (AII) and are useful in alleviating angiotensin induced hypertension constitute the subject matter of a tremendous amount of research.

PCT Application, International Publication Number WO 92/00977 published Jan. 23, 1992, discloses 4-alkylimidazole derivatives useful as angiotensin II antagonist antihypertensive agents.

Carini and Duncia, European Patent Application Publication Number (EPA) 0 253 310, published Jan. 20, 1988, discloses a class of imidazole angiotensin II antagonists useful for treatment of hypertension and congestive heart failure. The compounds are active when administered by intravenous injection. Several of the compounds are also orally active. The general disclosure encompasses certain 4-alkyl-2-propyl-1-[(2'-(1H-tetrazol-5-yl)biphenyl-4-yl)methyl]imidazoles substituted at the 5-position of the imidazole ring with halogen, nitro, trifluoromethyl or cyano.

Carini, Duncia and Wong, International Application Publication Number WO 89/06233, published Jul. 13, 1989, discloses the same class of imidazole angiotensin II antagonists and also discloses additional imidazole angiotensin II antagonists useful for treatment of hypertension and congestive heart failure. Some of the additionally-disclosed compounds are orally active. The general disclosure of WO 89/06233 encompasses the compounds of this invention, but the compounds of this invention are not specifically disclosed.

PCT Application, International Publication Number WO 91/00277 published Jan. 10, 1991, discloses substitutes imidazoles useful as AII blockers. The compounds describes have activity in treating hypertension and congestive heart failure.

PCT Application, International Publication Number WO 91/00281 published Jan. 10, 1991, describes fused-ring aryl substituted imidazoles useful as AII blockers. The compounds described have activity in treating hypertension and congestive heart failure.

European Patent Application Publication Number 0 434 249 A2 published Jun. 26, 1991 describes benzofuran derivatives useful in treatment or prophylaxis of hypertension and potentially useful for the treatment of cognitive disorders and other diseases such as renal failure, hyperaldosteronism, cardiac insufficiency, congestive heart failure, post-myocardial infarction, cerebrovascular disorders, glaucoma and disorders of intracellular homeostasis.

European Patent Application Publication Number 0 459 136 A1 published Apr. 12, 1991 describes benzimidazole derivatives having AII antagonistic activity and antihypertensive activity.

Compounds which inhibit AII such as imidazole carboxylic acid AII blockers can have poor absorption in the gastrointestinal tract. One way in which bioavailability of such compounds might be improved would involve designing a prodrug which would hydrolyze to the corresponding acid under physiological conditions whereby this hydrolysis would occur at some point after the prodrug has been absorbed in the gut thus liberating the parent compound without impairing its pharmacological activity.

SUMMARY OF THE INVENTION

In one embodiment this invention relates to a class of novel 5-imidazole carboxylic esters as represented by Formula I:

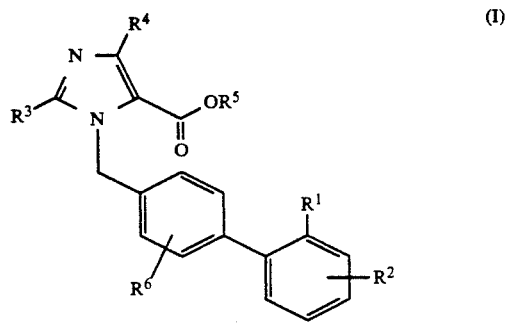

wherein
$R^1$ is —$CO_2H$ or

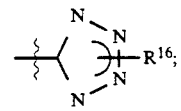

$R^2$ is
(a) H,
(b) C1–C5-alkyl,
(c) $C_1$–$C_5$-alkoxy,
(d) halo (F, Cl),
(e) phenyl;

$R^3$ is C1–C5-alkyl, C2–C5-alkenyl, C2–C5-alkynyl;

$R^4$ is
(a) H,
(b) halo (Cl, Br, I),
(c) C1–C6-alkyl,
(d) $C_vF_w$ where v=1 to 3 and w=1 to (2v+1);

$R^5$ is
(a) C1–C5-alkyl,
(b) C2–C5-alkenyl,
(c) C2–C5-alkynyl,
(d) —$(CH_2)_pNR^{12}R^{13}$,
(e) —$(CH_2)_sCH(R^7)(CH_2)_s$ $O_2CR^8$,
(f)

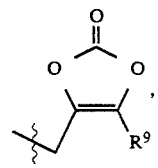

(g) —$(CH_2)_pCO_2R_{10}$,
(h)

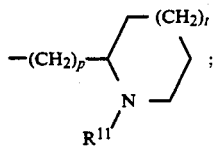

$R^6$ is
(a) H,
(b) halogen (F, Cl, Br, I),
(c) C1–C5-alkyl,
(d) —OH,
(e) C1–C4-alkoxy,
(f) —NO$_2$,
(g) —NR$^{12}$R$^{13}$,
(h) —NR$^{12}$COR$^{15}$,
(i) —NR$^{12}$CO$_2$R$^{15}$,
(j) —S(O)$_r$R$^{14}$ where r is 0, 1 or 2,
(h) —CO$_2$R$^{15}$,
(i) —C$_v$F$_w$ where v=1 to 3 and w=1 to (2v+1),
(J) —OC$_v$F$_w$ where v=1 to 3 and w=1 to (2v+1), or
(K) —CN;

$R^7$ is H or C1–C4-alkyl;

$R^8$ is
(a) H,
(b) C1–C5-alkyl,
(c) C1–C5-alkyl optionally substituted with a group consisting of:
  i) C1–C5-alkoxy,
  ii) aryl, wherein aryl is phenyl or napthyl optionally substituted with one or two substituents selected from the group consisting of halo (F, Cl, Br, I), C1–C4-alkyl, C1–C4-alkoxy, —NO$_2$, —S(O)$_r$(C1–C5-alkyl), —OH, —NR$^{12}$R$^{13}$, —CO$_2$R$^{15}$, and —C$_v$F$_w$ where v=1 to 3 and w=1 to (2v+1);

$R^9$ is
(a) C1–C5-alkyl,
(b) —C$_v$F$_w$ where v=1 to 3 and w=1 to (2v+1),
(c) C1–C5-alkyl optionally substituted with a group consisting of:
  i) C1–C5-alkoxy,
  ii) phenyl or phenyl substituted with at least one substituent selected from the group consisting of halo (F, Cl, Br, I), C1–C4-alkyl, C1–C4-alkoxy, —NO$_2$, —S(O)$_r$(C1–C4-alkyl), —OH, —NR$^{12}$R$^{13}$, —CO$_2$R$^{15}$, and —C$_v$F$_w$ where v=1 to 3 and w=1 to (2v+1),
  iii) benzyl or benzyl substituted with at least one substituent selected from the group consisting of halo (F, Cl, Br, I), C1–C4-alkyl, C1–C4-alkoxy, —NO$_2$, —S(O)$_r$(C1–C4-alkyl), —OH, —NR$^{12}$R$^{13}$, —CO$_2$R$^{15}$, and —C$_v$F$_w$ where v=1 to 3 and w=1 to (2v+1);

$R^{10}$ is
(a) phenyl or phenyl substituted with at least one substituent selected from the group consisting of halo (F, Cl, Br, I), C1–C4-alkyl, C1–C4-alkoxy, —NO$_2$, —S(O)$_r$(C1–C4-alkyl), —OH, —NR$^{12}$R$^{13}$, —CO$_2$R$^{15}$, and —C$_v$F$_w$ where v=1 to 3 and w=1 to (2v+1),
(b) benzyl or benzyl substituted with at least one substituent selected from the group consisting of halo (F, Cl, Br, I), C1–C4-alkyl, C1–C4-alkoxy, —NO$_2$, —S(O)$_r$(C1–C4-alkyl), —OH, —NR$^{12}$R$^{13}$, —CO$_2$R$^{15}$, and —C$_v$F$_w$ where v=1 to 3 and w=1 to (2v+1);

$R^{11}$ is H, C1–C5-alkyl or benzyl;
$R^{12}$ and $R^{13}$ are independently H, C1–C5-alkyl, phenyl or benzyl;
$R^{14}$ is CF$_3$, C1–C5-alkyl, or phenyl;
$R^{15}$ is H, C1–C5-alkyl, or NR$^{12}$R$^{13}$;
$R^{16}$ is H or CH$_2$O$_2$CC(CH$_3$)$_3$;
p is 1–5;
r is 0–2;
s and s' are 0–5;
t is 0 or 1;
or a pharmaceutically acceptable salt thereof.

In a second embodiment, this invention relates to pharmaceutical compositions comprising a pharmaceutically suitable carrier and a therapeutically effective amount of the compounds of this invention.

In a third embodiment, this invention concerns a method of treating hypertension in a warm-blooded animal comprising orally administering to the animal a therapeutically effective amount of a compound of the invention.

In a fourth embodiment, this invention concerns a method of treating congestive heart failure in a warm-blooded animal comprising orally administering to the animal a therapeutically effective amount of a compound of the invention.

DETAILED DESCRIPTION OF THE INVENTION

The compounds of this invention exhibit remarkable and unexpected potency as antihypertensive agents in comparison to the compounds specifically disclosed in EPA 0 253 310 and WO 89/06233 which have been tested.

More specifically, the compounds of the invention which have been tested all have equal or greater oral antihypertensive potency than any of the compounds specifically disclosed in EPA 0 253 310 and WO 89/06233 which have been tested.

The compounds of the invention are also highly active antihypertensive agents when administered by intravenous injection.

The compounds of the invention are 5-imidazole carboxylic ester having the general Formula I:

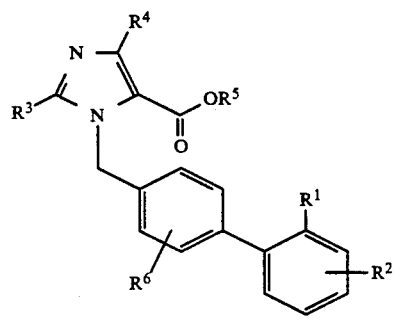

wherein
$R^1$ is —CO$_2$H or

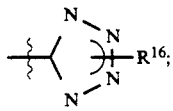

$R^2$ is
(a) H,
(b) C1-C5-alkyl,
(c) C1-C5-alkoxy,
(d) halo (F, Cl),
(e) phenyl;

$R^3$ is C1-C5-alkyl, C2-C5-alkenyl, C2-C5-alkynyl;

$R^4$ is
(a) H,
(b) halo (Cl, Br, I),
(c) C1-C6-alkyl,
(d) $C_vF_w$ where v=1 to 3 and w=1 to (2v+1);

$R^5$ is
(a) C1-C5-alkyl,
(b) C2-C5-alkenyl,
(c) C2-C5-alkynyl,
(d) $-(CH_2)_pNR^{12}R^{13}$,
(e) $-(CH_2)_sCH(R^7)(CH_2)_{s'}O_2CR^8$,
(f)

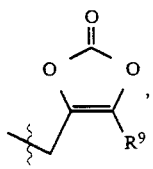

(g) $-(CH_2)_pCO_2R^{10}$,
(h)

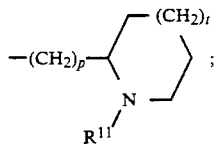

$R^6$ is
(a) H,
(b) halogen (F, Cl, Br, I),
(c) C1-C5-alkyl,
(d) $-OH$,
(e) C1-C4-alkoxy,
(f) $-NO_2$,
(g) $-NR^{12}R^{13}$,
(h) $-NR^{12}COR^{15}$,
(i) $-NR^{12}CO_2R^{15}$,
(j) $-S(O)_rR^{14}$ where r is 0, 1 or 2,
(h) $-CO_2R^{15}$,
(i) $-C_vF_w$ where v=1 to 3 and w=1 to (2v+1),
(J) $-OC_vF_w$ where v=1 to 3 and w=1 to (2v+1), or
(K) $-CN$;

$R^7$ is H or C1-C4-alkyl;

$R^8$ is
(a) H,
(b) C1-C5-alkyl,
(c) C1-C5-alkyl optionally substituted with a group consisting of:
i) C1-C5-alkoxy,
ii) aryl, wherein aryl is phenyl or napthyl optionally substituted with one or two substituents selected from the group consisting of halo (F, Cl, Br, I), C1-C4-alkyl, C1-C4-alkoxy, $-NO_2$, $-S(O)_r(C1-C>5-alkyl)$, $-OH$, $-NR^{12}R^{13}$, $-CO_2R^{15}$, and $-C_vF_w$ where v=1 to 3 and w=1 to (2v+1);

$R^9$ is
(a) C1-C5-alkyl,
(b) $-C_vF_w$ where v=1 to 3 and w=1 to (2v+1),
(c) C1-C5-alkyl optionally substituted with a group consisting of:
i) C1-C5-alkoxy,
ii) phenyl or phenyl substituted with at least one substituent selected from the group consisting of halo (F, Cl, Br, I), C1-C4-alkyl, C1-C4-alkoxy, $-NO_2$, $-S(O)_r(C1-C4-alkyl)$, $-OH$, $-NR^{12}R^{13}$, $-CO_2R^{15}$, and $-C_vF_w$ where v=1 to 3 and w=1 to (2v+1),
iii) benzyl or benzyl substituted with at least one substituent selected from the group consisting of halo (F, Cl, Br, I), C1-C4-alkyl, C1-C4-alkoxy, $-NO_2$, $-S(O)_r(C1-C4-alkyl)$, $-OH$, $-NR_{12}R_{13}$, $-CO_2R^{15}$, and $-C_vF_w$ where v=1 to 3 and w=1 to (2v+1);

$R^{10}$ is
(a) phenyl or phenyl substituted with at least one substituent selected from the group consisting of halo (F, Cl, Br, I), C1-C4-alkyl, C1-C4-alkoxy, $-NO_2$, $-S(O)_r(C1-C4-alkyl$, $-OH$, $-NH^{12}R^{13}$, $CO_2R^{15}$, and $-C_vF_w$ where v=1 to 3 and w=1 to (2v+1),
(b) benzyl or benzyl substituted with at least one substituent selected from the group consisting of halo (F, Cl, Br, I), C1-C4-alkyl, C1-C4-alkoxy, $-NO_2$, $-S(O)_r(C1-C4-alkyl)$, $-OH$, $-NR^{12}R^{13}$, $-CO_2R^{15}$, and $-C_vF_w$ where v=1 to 3 and w=1 to (2v+1);

$R^{11}$ is H, C1-C5-alkyl or benzyl;
$R^{12}$ and $R^{13}$ are independently H, C1-C5-alkyl, phenyl or benzyl;
$R^{14}$ is $CF_3$, C1-C5-alkyl, or phenyl;
$R^{15}$ is H, C1-C5-alkyl, or $NR^{12}R^{13}$;
$R^{16}$ is H or $CH_2O_2CC(CH_3)_3$;
p is 1-5;
r is 0-2;
s and s' are 0-5;
t is 0 or 1;
or a pharmaceutically acceptable salt thereof.

Preferred for their antihypertensive activity are novel compounds of Formula I above wherein $R^1$ is

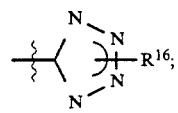

$R^2$ is H;
$R^3$ is C1-C5-alkyl;
$R^5$ is
(a) $-(CH_2)_sCH(R^7)(CH_2)_{s'}O_2CR^8$,
(b)

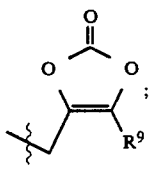

$R^6$ is H;
$R^7$ is H;
$R^8$ is
  (a) H,
  (b) C1–C5-alkyl,
  (c) C1–C5-alkoxy,
  (d) C1–C5-alkyl optionally substituted with a group consisting of:
    i) C1–C5-alkoxy;
$R^9$ is
  (a) C1–C5-alkyl;
  (b) C1–C5-alkyl optionally substituted with a group consisting of:
    i) C1–C5-alkoxy,
    ii) phenyl or phenyl substituted with at least one substituent selected from the group consisting of halo (F, Cl, Br, I), alkyl, C1–C5-alkoxy, —OH,
    iii) benzyl or benzyl substituted with at least one substituent selected from the group consisting of halo (F, Cl, Br, I), C1–C5-alkoxy, —OH;
p is 1;
s is 1;
s' is 0.

Most preferred are compounds having the Formula I above wherein
$R^1$ is

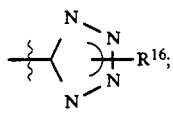

$R^2$ is H;
$R^3$ is C1–C5-alkyl;
$R^5$ is —(CH$_2$)$_s$CH(R$^7$)(CH$_2$)$_s$O$_2$CR$^8$;
$R^7$ is H;
$R^8$ is
  (a) C1–C5-alkoxy,
  (b) C1–C5-alkyl,
  (c) C1–C5-alkyl optionally substituted with a group consisting of:
    i) C1–C5-alkoxy;
p is 1;
s is 1.

Specifically preferred are the following:

Trimethylacetoxymethyl 4-ethyl-2-propyl-1-[[2'-(tetrazol-5-yl)biphenyl-4-yl]methyl]imidazole-5-carboxylate;
Methoxycarbonyloxymethyl 4-ethyl-2-propyl-1-[[2'-(tetrazol-5-yl)biphenyl-4-yl]methyl]imidazole-5-carboxylate;
t-Butoxycarbonyloxymethyl 4-ethyl-2-propyl-1-[[2'-(tetrazol-5-yl)biphenyl-4-yl]methyl]imidazole-5-carboxylate;
1-(Methoxycarbonyl)ethyl 4-ethyl-2-propyl-1-[[2'-(tetrazol-5-yl)biphenyl-4-yl]methyl]imidazole-5-carboxylate.

This invention also relates to pharmaceutical compositions containing these novel imidazole carboxylic acids and pharmaceutical methods using them.

Pharmaceutically acceptable salts include both the metallic (inorganic) salts and organic salts; a list of which is given in Remington's Pharmaceutical Science, 7th Edition, page 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium and ammonium salts.

Also within the scope of this invention are pharmaceutical compositions comprising a suitable pharmaceutical carrier and a compound of Formula I to treat hypertension or congestive heart failure.

The disclosure of all publications and references mentioned herein are hereby incorporated by reference unless indicated otherwise.

SYNTHESIS

The compounds of Formula I can be prepared using the reagents and materials described herein. The reactions are performed in a solvent appropriate to the reagents and materials employed and suitable for the transformation being effected.

Synthesis of the terminal, substituted phenyl ring of the biphenyl region of compounds having the structure of Formula I above is described in Scheme 1. Carboxylic acids (4), which are commercially available, can be protected with 2-amino-2-methylpropanol to form oxazolines (5) using the procedure described in *J. Am. Chem. Soc.* 97: 7383 (1975). Ortho lithiation of the oxazoline with butyl lithium followed by quenching with triisopropyl borate and borate hydrolysis with aqueous acetic acid gives phenyl boronic acid (6) as is described in U.S. Pat. No. 5,130,439 issued Jul. 14, 1992.

Similarly, nitriles (5) which are also commercially available can be treated with tributyl tin chloride and sodium azide to prepare the corresponding tin tetrazole which is used in situ. Tributyl tin is removed using sodium hydroxide and the resulting tetrazole is protected with trityl chloride. As discussed above, the corresponding tetrazolyl phenyl boronic acids (7) are produced using ortho lithiation with butyl lithium, quenching with triisopropyl borate and hydrolysis with aqueous acetic acid as is described in U.S. Pat. No. 5,130,439 issued Jul. 14, 1992.

Scheme 1

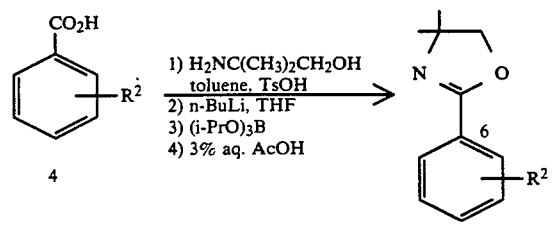

-continued
Scheme 1

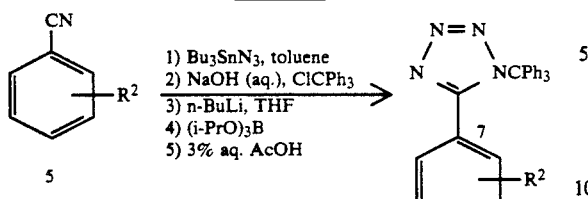

Biphenyl compounds (10) or (12) can be prepared using the procedure illustrated in Scheme 2 below. Boronic acids (6) or (7) are coupled to halides (8) using tetrakis(triphenylphosphine) palladium catalyst in toluene and 2M sodium carbonate to produce biphenyl compounds (9(a,b)) as described in *Syn. Comm.*, 11: 513 (1981). Bromination of biphenyl compounds (9a) with N-bromosuccinimide (NBS) using azobisisobutyrylnitrile (AIBN) as a catalytic initiator according to the procedure described in U.S. Pat. No. 4,820,843 issued Apr. 11, 1989 produces the corresponding bromide compounds (10). Alternatively, compound (9b) can be hydrolyzed with aqueous mineral acid then reprotected with isobutylene and a catalytic amount of sulfuric acid to produce t-butyl esters (11) which can be brominated using NBS to produce the corresponding bromides (12).

Scheme 2

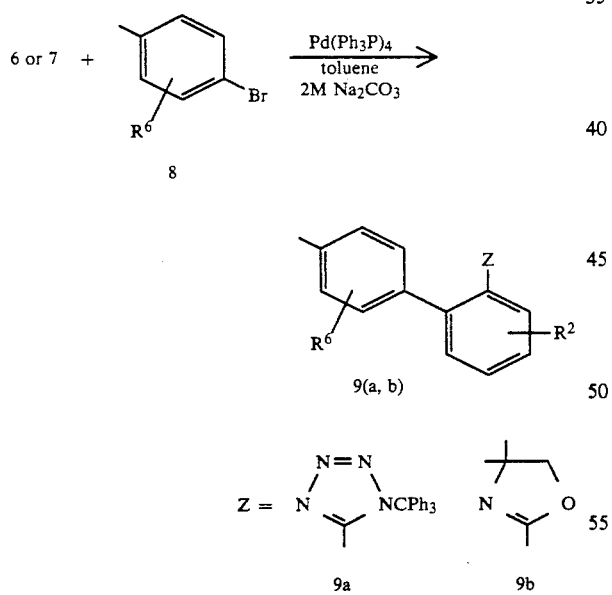

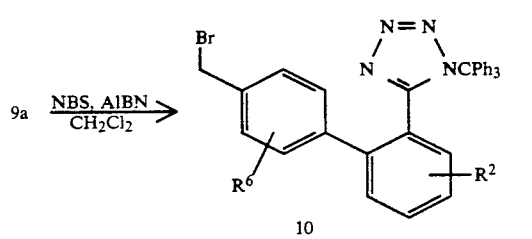

-continued
Scheme 2

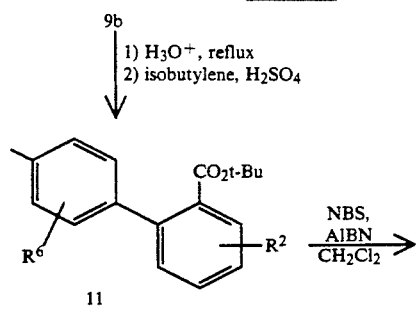

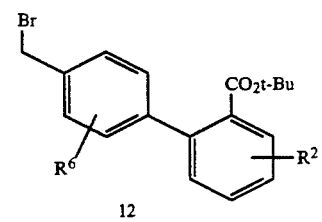

Synthesis of the imidazole portion of the compounds of Formula I are described in Scheme 3. Commercially available terminal acetylenes (13) are deprotonated with either n-butyl lithium or ethyl magnesium bromide and quenched with the appropriated chloroformate to produce esters (14). Imidazoles (3) are made by reacting these esters (14) with amidoximes, prepared according to the procedure described in Cancer Research 38: 1291 (1978), followed by addition of xylene and refluxing for several hours.

Scheme 3

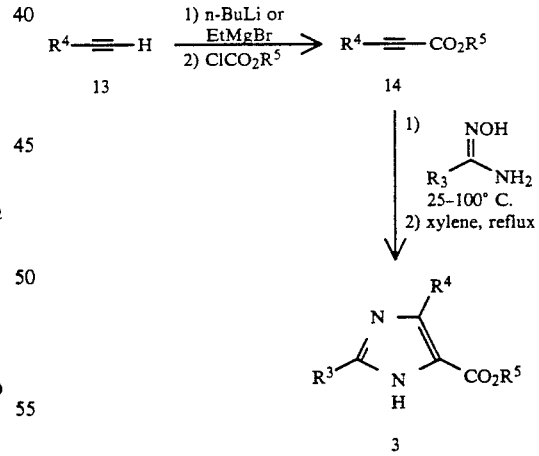

An alternative approach is set forth in Scheme 4. This alternative approach is desirable if a larger quantities of the imidazole (3) are needed. Commercially available β-ketoesters are treated with sodium nitrite in aqueous hydrochloric acid to make oximes (16). Condensation with ammonia in methanol provides N-hydroxyimidazoles (17). Deoxygenation of the n-hydroxyimidazoles (17) with triisopropylphosphite produces the corresponding imidazoles (3).

Scheme 4

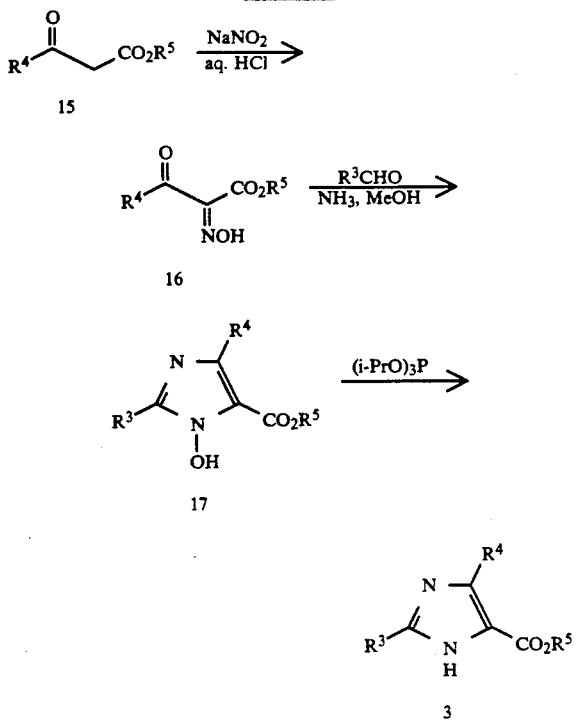

Preparation of compounds of Formula I wherein $R^5$ is H are set forth in Scheme 5. Imidazoles (3) are alkylated with bromomethylbiphenyl compounds (10) using potassium carbonate in dimethylformamide (DMF) as described in PCT Patent Application having International Publication Number WO 92/009777 published Jan. 23, 1992. These alkylations produce a mixture of regioisomers in which the major product is the regioisomer corresponding to compound (18). Carboxylic acids (2) are obtained by removing the trityl protecting groups using aqueous sodium hydroxide followed by an aqueous acid such as 1 N hydrochloric acid.

Scheme 5

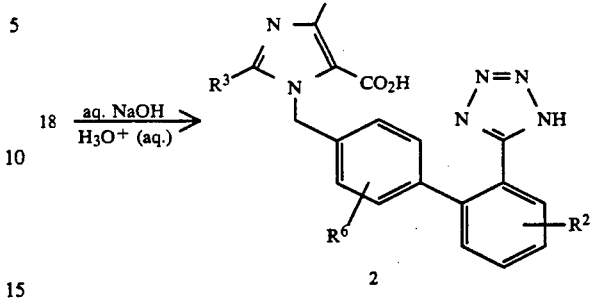

Alkylation of carboxylic acids (2) is described in Scheme below. The tetrazole compounds (2) is protected with a trityl group by treating with trityl chloride in the presence of triethylamine to produce the corresponding tetrazoles (20) which are then alkylated with the appropriate alkyl halide using a catalytic amount of potassium iodide in the presence of potassium carbonate. The tetrazole is deprotected by treating with hydrochloric acid in methanol to produce tetrazoles (21).

An alternative approach involves alkylating compounds (20) with the appropriate alkyl halide and triethylamine in tetrahydrofuran (THF). Deprotection with silica gel in methanol produces tetrazoles (21).

Scheme 6

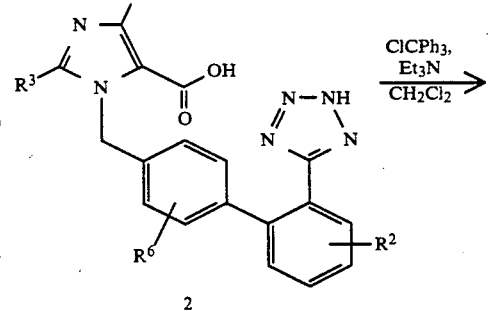

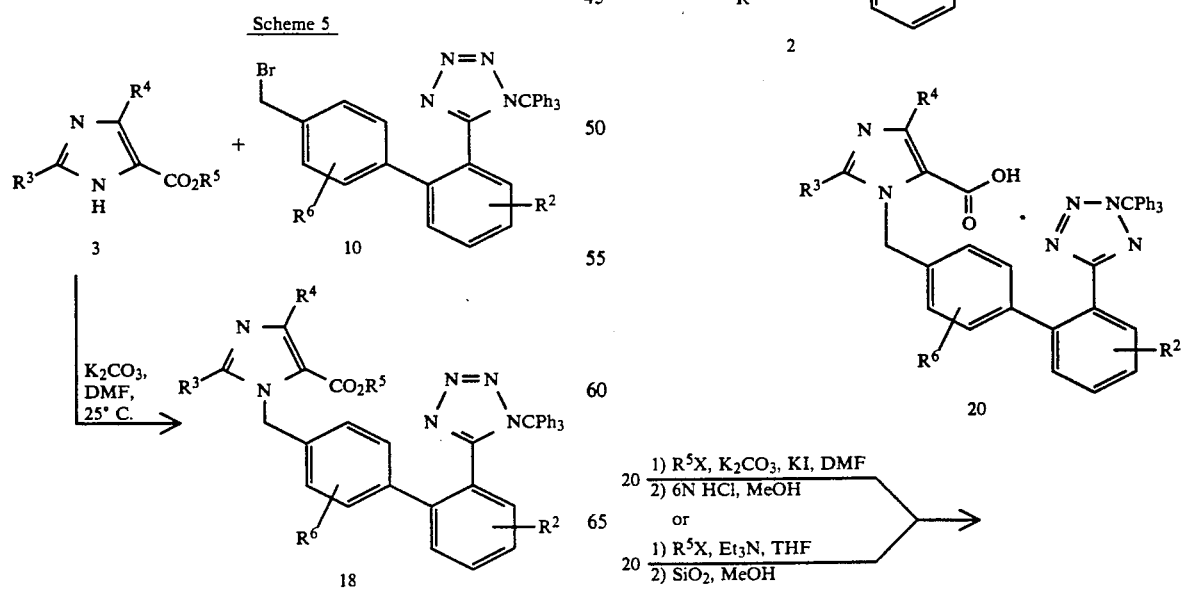

-continued
Scheme 6

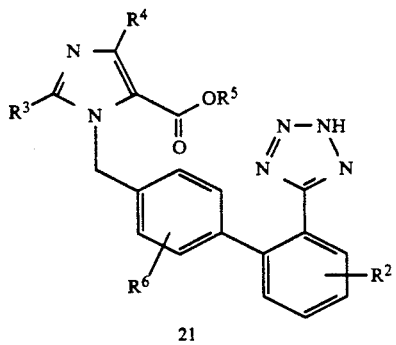
21

-continued
Scheme 8

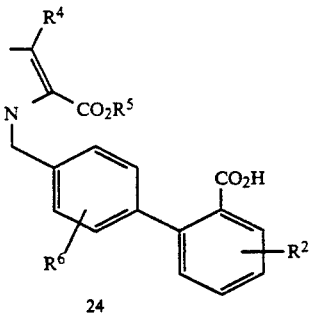
24

If the trityl protecting group is not used then alkylation of compounds (2) with the appropriate alkyl halide occurs at both the carboxylic acid and the tetrazole as shown in Scheme 7 to produce compounds (22).

Preparation of compounds of Formula I where $R^5$ is $CH_2NR^{12}R^{13}$ can be prepared as outlined in Scheme 9 below. The appropriate imonium salt is added to the carboxylic acid (2) or (12) to form the corresponding amine which can then be deprotected to give the desired compounds.

Scheme 7

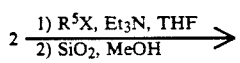

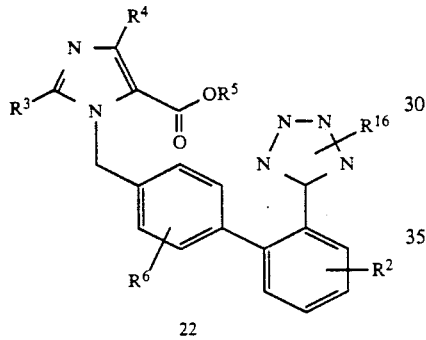
22

Scheme 9

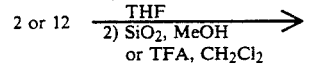

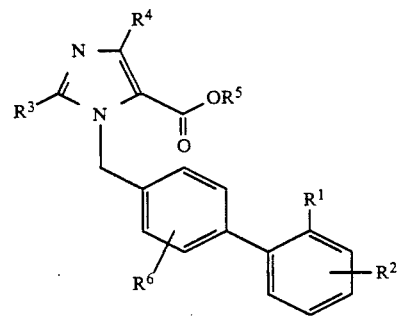
I ($R^5 = CH_2NR^{12}R^{13}$)

Alkylation of imidazoles (3) with bromides (12) followed by monohydrolysis with 1 N sodium hydroxide in methanol produces esters (23) which can then be alkylated with the appropriate alkyl halide in triethylamine and THF. Deprotection with trifluoroacetic acid (TFA) in methylene chloride produces the acids (24).

Preparation of the appropriate alkyl halides can found in Curran and Ross, U.S. Pat. No. 4,914,091, issued Apr. 3, 1990, Journal of Antibiotics 40, 370–84, 1987, and Chemical and Pharmaceutical Bulletin 32, 2241, (1984).

The compounds of this invention and their preparation can be understood further by the following examples, which do not constitute a limit of the invention. In these examples, unless otherwise indicated, all temperatures are in degrees centigrade and parts and percentages are by weight. The disclosures of all references cited herein are hereby incorporated by reference unless otherwise indicated.

EXAMPLE 1

Preparation of Propyl 4-ethyl-2-propyl-1-[[2'-(tetrazol-5-yl)biphenyl-4-yl]methyl]imidazole-5-carboxylate Part A: Preparation of Butyramidoxime 347.5 g of hydroxylamine hydrochloride was dissolved in 3500 mL methanol and cooled to 0° C. A 50% aqueous solution of sodium hydroxide (412 g NaOH) was slowly added and allowed to stir at room tempera-

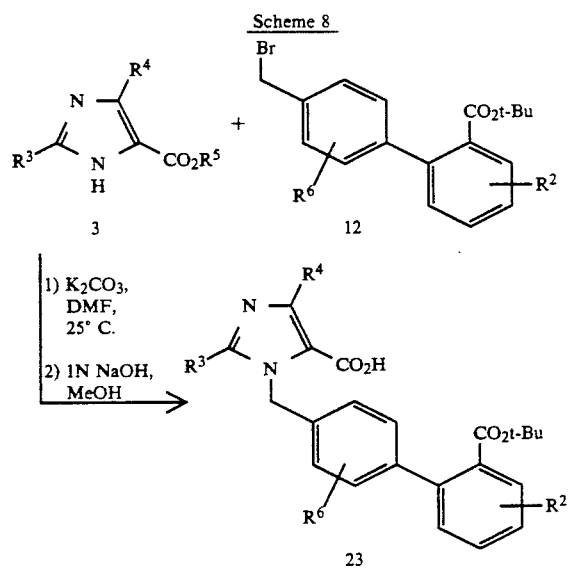
Scheme 8
23 ture for 30 minutes. The precipitate was filtered and 435 mL of butyronitrile was added to the filtrate. The mixture was stirred for an additional 16 hours and 500 mL water was added. The reaction was evaporated to remove the methanol, extracted with ethyl acetate, the organic extracts dried with $Na_2SO_4$ and evaporated to give 306 g product.

$^1$H-NMR (CDCl$_3$) δ 0.96 (t, 3H), 1.59 (t, 2H), 2.12 (t, 2H), 4.56 (bs, 2H).

Part B: Preparation of Methyl 4-ethyl-2-propylimidazole-5-carboxylate 93 g of methyl pentynoate and 82 g butyramidoxime are mixed together without solvent and heated to 50° C for 24 hours. 400 mL xylene was added and water was azaeotropically removed for 6 hours. The reaction was then distilled (140° C. at 0.2 torr) to give 44 g product.

$^1$H-NMR(CDCl$_3$) δ 0.99 (t, 3H), 1.15 (t, 3H), 1.65 (m, 2H), 2.71 (m, 2H), 2.97 (q, 2H), 3.87 (s, 3H).

Part C: Preparation of 2-(2'-Triphenylmethyl-2'H-tetrazol-5'-yl)phenylboronic acid To a 22 L flask under nitrogen purge was charged 8.25 L acetone, followed by 1.1 kg 5-phenyltetrazole. Trietyylamine (800 g) was added in such a rate that the temperature was maintained below 35° C. with some cooling. Solid trityl chloride was charged to this suspension in five 440 g portions. The temperature was maintained below 35° C. An additional 1.38 L acetone was added to the reaction which was then maintained at 25° to 30° C with stirring for 2 hours. Water (2.2 L) was added and the mixture was chilled to 15° to 20° C. The solid was collected by filtration; the filter cake was rinsed with 1.65 L 50% acetone-water followed by excess amount of water. The wet cake was re-slurried in 8 L acetone and 8 L of water was added slowly. The suspension was stirred for 1 hour then filtered. The filter cake was rinsed with 3 to 5 L of water. The white solid was dried in a vacuum oven at 40°–45° C. to a constant weight of 3.0 kg, mp 158°–160° C.

To a dry 12 L flask under nitrogen purge was charged 3 19 L of dry tetrahydrofuran With agitation, 398 g of 5-phenyl-1-trityl-tetrazole prepared above was charged. The system was evacuated and released to nitrogen three times and then cooled to −20° C. A solution of n-butyl lithium in heptane (1.6 M, 477 g) was then added to the reaction mixture while maintaining the temperature at −15° C. to −20° C. The resultant deep red solution was stirred at −5° C. for 1 hour during which time the lithium salt crystallized out. The solid suspension was cooled to −25° C. again and 333 g triisopropylborate was charged at a temperature range of −20° C. to −25° C. After the addition, the mixture was allowed to warm to 20° C. without heating. About 2.5 L of solvent was removed by vacuum distillation while the pot temperature was kept below 40° C. To the mixture was then added 2.66 L of 3% acetic acid and the resultant suspension was stirred for 1 hour. The white solid was collected by filtration. The solid cake was rinsed with 1.5 L of 20% tetrahydrofuran in water, followed by 3 L of water. The solid was dried under vacuum at room temperature to a constant weight of 502.3 g, mp 142°–146° C. (dec.).

Part D: Preparation of 2'-(N-triphenylmethyl-(1H-tetrazol-5-yl))biphenyl-4-yl)methane 1.02 g of 4-bromotoluene, 2.16 g of phenyl boronic acid, 1.38 g potassium carbonate, 0.15 g tetrabutyl ammonium bromide and 1 mL water are mixed together. 0.18 g of tetrakistriphenylphosphine palladium is added and the vacuum purged with nitrogen three times. The reaction was refluxed for 6 hours, cooled and diluted with a mixture of toluene and water. The mixture was separated and the aqueous layer was extracted with toluene, dried with $MgSO_4$, filtered and evaporated to give 1.87g of crude product. This material was taken on without purification.

$^1$H-NMR(CDCl$_3$) δ 2.4 (s, 3H), 6.9 (d, 6H), 7.22–7.5 (m, 16H), 7.97 (m, 1H).

Part E: Preparation of 2'-(N-triphenylmethyl-(1H-tetrazol-5-yl))biphenyl-4-yl)methyl bromide 2'-(N-triphenylmethyl-(1H-tetrazol-5-yl))biphenyl-4-yl)methane (52.07 g, 109 mmol, 1 eq), N-bromosuccinimide (19.4 g, 109 mmol, 1 eq), benzoyl peroxide (1.0 g) and carbon tetrachloride (300 mL) were mixed and refluxed for 2.5 hours. The reaction was cooled to room temperature and the succinimide filtered. The filtrate was concentrated and the residue triturated with ether to yield a first crop of 36.0 g of product. This material was suitable for further transformation.

mp 129.5°–133.0° C. (dec.).

$^1$H-NMR(CDCl$_3$) δ 4.37 (s, 2H), 6.9 (d, 6H), 7.22–7.5 (m, 16H), 7.97 (m, 1H).

Part F: Preparation of Methyl 4-ethyl-2-propyl-1-[[2'-(N-triphenylmethyl(tetrazol-5-yl))biphenyl-4-yl]methyl]imidazole-5-carboxylate 0.053 g of methyl 4-ethyl-2-propylimidazole-5-carboxylate, 0.12 g 2'-(N-triphenylmethyl-(1H-tetrazol-5-yl))biphenyl-4-yl)methyl bromide and 0.38 g potassium carbonate were dissolved/suspended in 10 mL DMF. The reaction was stirred overnight and then evaporated. The crude oil was chromatographed with ethyl acetate/hexanes (3:7) to give 0.14 g of the desired regioisomer.

$^1$H-NMR(CDCl$_3$) δ 0.96 (t, 3H), 1.21 (t, 3H), 1.67 (m, 2H), 2.58 (t, 2H), 2.85 (q, 2H), 3.77 (s, 3H), 5.42 (s, 2H), 6.82 (d, 2H), 6.92 (d, 6H), 7.22–7.5 (m, 14H), 7.92 (m, 1H).

Part G: Preparation of 4-Ethyl-2-propyl-1-[[2'-(tetrazol-5-yl)biphenyl-4-yl]methyl]imidazole-5-carboxylic acid 0.97 g of methyl 4-ethyl-2-propyl-1-[[2'-(N-triphenylmethyl(tetrazol-5-yl))biphenyl-4-yl]methyl]imidazole-5-carboxylate is dissolved in 2 mL methanol and added to 10 mL 3N potassium hydroxide. This was allowed to reflux for 6 hours then cooled to room temperature. The mixture was extracted with $CH_2Cl_2$ then acidified with 1 N HCl to pH 4 to give 0.52 g of product which precipitated and was isolated by filtration.

$^1$H-NMR(CDCl$_3$) δ 0.93 (t, 3H), 1.31 (t, 3H), 1.66 (m, 2H), 2.57 (t, 2H), 2.8 (q, 2H), 5.44 (s, 2H), 6.86 (d, 2H), 7.20 (d, 2H), 7.25–7.5 (m, 3H), 7.88 (m, 1H).

Part H: Preparation of 4-Ethyl-2-propyl-1-[[2'-(N-triphenylmethyl(tetrazol-5-yl))biphenyl-4-yl]methyl]imidazole-5-carboxylic acid A mixture of 7.5 g of 4-ethyl-2-propyl-1-[[2'-(tetrazol-5-yl)biphenyl-4-yl]methyl]imidazole-5-carboxylic acid, 5.17 g trityl chloride and 1.92 g triethylamine in 50 mL CH$_2$Cl$_2$ is stirred overnight. After water addition and acidification with 1N HCl to pH 3, the mixture was separated and the organic phase was extracted with CH$_2$Cl$_2$/ethyl acetate (1:1). The mixture was dried with Na$_2$SO$_4$, suction filtered and the solvent evaporated. 6.46 g of product was obtained after flash chromatography with ethyl acetate.

$^1$H-NMR(CDCl$_3$) δ 0.93 (t, 3H), 1.22 (t, 3H), 1.62 (m, 2H), 2.51 (t, 2H), 2.92 (q, 2H), 5.4 (s, 2H), 6.76 (d, 2H), 6.91 (m, 6H), 7.04 (d, 2H), 7.2–7.35 (m, 10H), 7.43 (m, 2H), 7.89 (m, 1H).

Part I: Preparation of Propyl 4-ethyl-2-propyl-1-[[2'-(N-triphenylmethyl(tetrazol-5-yl))biphenyl-4-yl]methyl]imidazole-5-carboxylate 1.32 g of 4-ethyl-2-propyl-1-[[2'-(N-triphenylmethyl(-tetrazol-5-yl))biphenyl-4-yl]methyl]imidazole-5-carboxylic acid, 0.39 mL of iodopropane and 0.55 g potassium carbonate were added to 6 mL DMF. The reaction was allowed to stir for 24 hours then diluted with 12 mL water and 90 mL ethyl acetate. The organic layer was separated and washed five times with water, once with brine and dried with MgSO$_4$. Chromatography with a gradient from 5 to 50% ethyl acetate in hexane gave 0.96 g of desired product.

$^1$H-NMR(CDCl$_3$) δ 0.85 (t, 3H), 0.95 (t, 3H), 1.26 (t, 3H), 1.65 (m, 4H), 2.46 (t, 2H), 2.7 (q, 2H), 4.1 (t, 2H), 5.4 (s, 2H), 6.77 (m, 2H), 6.9 (m, 6H), 7.07 (m, 2H), 7.28 (m, 9H), 7.48 (m, 2H), 7.92 (m, 1H).

Part J: Preparation of Propyl 4-ethyl-2-propyl-1-[[2'-(tetrazol-5-yl)biphenyl-4-yl]methyl]imidazole-5-carboxylate 0.96 g of propyl 4-ethyl-2-propyl-1-[[2'-(N-triphenylmethyl(tetrazol-5-yl))biphenyl-4-yl]methyl]imidazole-5-carboxylate was dissolved in 22 mL of methanol and then 4.8 g silica gel and 6 drops of 6N HCl were added. The gel was filtered away after 3 days and the resulting silica was washed with CH$_2$Cl$_2$ and then ethyl acetate. The combined organic solutions were evaporated and the residue was chromatographed with a gradient of 0 to 5% methanol in chloroform to provide 0.25 g of the title compound.

$^1$H-NMR(CDCl$_3$) δ 0.8–0.95 (m, 9H), 1.45–1.65 (m, 4H), 2.15 (t, 2H), 2.48 (t, 2H), 4.07 (t, 2H), 5.4 (s, 2H), 6.74 (m, 2H), 7.05 (m, 2H), 7.27 (m, 1H), 7.48 (m, 2H), 7.77 (m, 1H).

EXAMPLE 2

Preparation of (N,N-Dimethylamino)methyl 4-ethyl-2-propyl-1-[[2'-(tetrazol-5-yl)biphenyl-4-yl]methyl]imidazole-5-carboxylate 4-ethyl-2-propyl-1-[[2'-(N-triphenylmethyl(tetrazol-5-yl))biphenyl-4-yl]methyl]imidazole-5-carboxylic acid is treated with Eschenmoser's salt in THF at room temperature overnight to give the title compound.

EXAMPLE 3

Preparation of Acetoxymethyl 4-ethyl-2-propyl-1-[[2'-tetrazol-5-yl)biphenyl-4-yl]methyl]imidazole-5-carboxylic

Part A: Preparation of Chloromethyl Acetate 3.90 g potassium acetate was suspended in 50 mL DMF. 7 g Iodochloromethane was added and the mixture stirred for 2.5 hours. 50 mL CH$_2$Cl$_2$ was added and the solution was washed six times with water and dried with MgSO$_4$. Suction filtration and evaporation of the filtrate provided 3.1 g of the ester.

$^1$H-NMR(CDCl$_3$) δ 2.11 (s, 3H), 5.31 (s, 2H).

Part B: Preparation of Acetoxymethyl 4-ethyl-2-propyl-1-[[2'-(tetrazol-5-yl)biphenyl-4-yl]methyl]imidazole-5-carboxylate 0.37 g of 4-ethyl-2-propyl-1-[[2'-(N-triphenylmethyl(-tetrazol-5-yl))biphenyl-4-yl]methyl]imidazole-5-carboxylic acid was dissolved in 5 mL THF and 0.5 g chloromethyl acetate and 0.5 mL triethylamine were added. The resulting solution was stirred overnight. The solvent was evaporated and the residue dissolved in methanol with 0.25 mL acetic acid and stirred 8 hours with 10 g silica gel. The mixture was evaporated and the residue on the gel was flash chromatographed with MeOH/CH$_2$Cl$_2$ (1:9) to provide 0.124 g of the title compound.

$^1$H-NMR(CDCl$_3$) δ 0.94 (t, 3H), 1.23 (t, 3H), 1.63 (m, 2H), 2.09 (s, 3H), 2.53 (t, 2H), 2.95 (q, 2H), 5.42 (bs, 4H), 6.76 (d, 2H), 7.04 (d, 2H), 7.35 (m, 1H), 7.43 (m, 2H), 7.79 (m, 1H).

EXAMPLE 4

Preparation of Isobutyryloxymethyl 4-ethyl-2-propyl-1-[[2'-(tetrazol-5-yl)biphenyl-4-yl]methyl]imidazole-5-carboxylate

Part A: Preparation of Chloromethyl Isobutyrate

Several drops of 1.0 M ZnCl$_2$ in Et$_2$O solution was added to a mixture of 10.48 mL of isobutyryl chloride and 3.00 g of paraformaldehyde. The reaction exothermed and the paraformaldehyde dissolved. The mixture was stirred overnight at room temperature then in a 90° C. oil bath for 4 hours. Distillation directly out of the reaction flask provided 6.14 g of the product (bp 137°–39° C).

$^1$H-NMR(CDCl$_3$) δ 1.12 (d, 6H), 2.54 (m, 1H), 5.64 (s, 2H).

Part B: Preparation of Isobutyryloxymethyl 4-ethyl-2-propyl-1-[[2'-(N-triphenylmethyl(tetrazol-5-yl))biphenol-4-yl]methyl]imidazole-5-carboxylate 0.2490 g KI in one portion was added to a mixture of 0.6588 g 4-ethyl-2-propyl-1-[[2'-(N-triphenylmethyl(tetrazol-5-yl))biphenyl-4-yl]methyl]imidazole-5-carboxylic acid, 0.2049 g chloromethyl isobutyrate, and 0.1382 g K$_2$CO$_3$ in 3 mL DMF. The mixture was stirred overnight at room temperature under Ar. The reaction was then partitioned between 8 mL H$_2$O and 40 mL EtOAc. The organic layer was washed once with ice cold 0.1 N sodium thiosulfate, once with H$_2$O, once with brine and dried with MgSO$_4$. After suction filtration and evaporation of the filtrate, flash chromatography with 25% EtOAc/hexanes provided 0.46 g of the desired product.

$^1$H-NMR(CDCl$_3$) δ 0.88 (t, 3H), 1.13 (d, 6H), 1.25 t, 3H), 1 68 (m, 2H), 2 45–2.60 (m, 3H), 1 93 (q, 2H), 5.41

(s, 2H), 5 80 (s, 2H), 6.76 (m, 2H), 6.93 (m, 6H), 7.08 (m, 2H), 7.2–7 5 (m, 12H), 7.90 (m, 1H).

Part C: Preparation of Isobutyryloxymethyl 4-ethyl-2-propyl-1-[[2'-(tetrazol-5-yl)biphenyl-4-yl]methyl]imidazole-5-carboxylate To a solution of 0.46 g isobutyryloxymethyl 4-ethyl-2-propyl-1-[[2'-(N-triphenylmethyl(tetrazol-5-yl))biphenyl-4-yl]methyl]imidazole-5-carboxylate in 10 mL MeOH was added 1 5 mL glacial acetic acid and the mixture stirred 2 days at room temperature. The reaction was evaporated to near dryness and the residue purified by flash chromatography using a 0% to 5% MeOH/CHCl$_3$ gradient. There was obtained 0.250 g of the title compound.

$^1$H-NMR(CDCl$_3$) δ 0.85 (2t, 6H), 1.08 (d, 6H), 1.55 (m, 2H), 2.21 (t, 2H), 2.41–2.59 (m, 3H), 5.43 (s, 2H), 5.78 (s, 2H), 6.73 (m, 2H), 7.03 (m, 2H), 7.4–7 68 (m, 3H), 7.78 (m, 1H).

EXAMPLE 5

Preparation of Trimethylacetoxymethyl 4-ethyl-2-propyl-1-[[2'-(tetrazol-5-yl)biphenyl-4-yl]methyl]imidazole-5-carboxylate 0.36 g of the title compound were obtained using the procedure described in Example 4 above using 0.242 g chloromethylpivalate.

$^1$H-NMR(CDCl$_3$) δ 0.88 (t, 3H), 1.18 (s, 9H), 1.22 (t, 3H), 1.65 (m, 2H), 2.5 (m, 2H), 2.9 (q, 2H), 5.41 s, 2H), 5.81 (s, 2H), 6.75 (d, 2H), 7.04 (d, 2H), 7.2–7.35 (m, 2H), 7.44 (m, 1H), 7.9 (m, 1H).

EXAMPLE 6

Preparation of Trimethylacetoxymethyl 4-ethyl-2-propyl-1-[[2'-(N-trimethylacetoxymethyl(tetrazol-5-yl))biphenyl-4-yl]methyl]imidazole-5-carboxylate 0.8 g of 4-ethyl-2-propyl-1-[[2'-(tetrazol-5-yl)biphenyl-4-yl]methyl]imidazole-5-carboxylic acid was dissolved in 10 mL THF and 0.5 g chloromethyl pivalate and 2 mL triethylamine were added. The resulting solution was stirred overnight. The solvent was evaporated and the residue was flash chromatographed with MeOH/CH$_2$Cl$_2$ (1:9) to provide 0.257 g of the title compound.

$^1$H-NMR(CDCl$_3$) δ 0.87 (t, 3H), 1.18 (s, 18H), 1.22 (t, 3H), 1.71 (m, 2H), 2.62 (m, 2H), 2.87 (q, 2H), 5.51 (s, 2H), 5.88 (s, 2H), 6.39 (s, 2H), 6.89 (d, 2H), 7.1 (d, 2H), 7.2–7.35 (m, 3H), 7.82 (m, 1H).

EXAMPLE 7

Preparation of Methoxycarbonyloxymethyl 4-ethyl-2-propyl-1-[[2'-tetrazol-5-yl)biphenyl-4-yl]methyl]imidazole-5-carboxylate Part A: Preparation of Chloromethyl Methyl Carbonate 1.22 ML MeOH was added slowly to a suspension of 1.29 g chloromethyl chloroformate and 1.52 g K$_2$CO$_3$ in 50 mL CH$_2$Cl$_2$. The reaction was stirred overnight at room temperature then suction filtered through glass fiber paper, washing with CH2Cl2. Evaporation of the filtrate provided 1.12 g of the product as an oil which was used without further purification.

$^1$H-NMR(CDCl$_3$): 3.88 (s, 3H), 5.75 (s, 2H).

Part B: Preparation of Methoxycarbonyloxymethyl 4-ethyl-2-propyl-1-[[2'-(N-triphenylmethyl(tetrazol-5-yl))biphenyl-4-yl[methyl[imidazole-5-carboxylate 0.44 g of the title product was obtained after chromatography (EtOAc) from 0.66 g 4-ethyl-2-propyl-1-[[2'-(N-triphenylmethyl(tetrazol-5-yl))biphenyl-4-yl]methyl]imidazole-5-carboxylic acid, 0.19 g chloromethyl methyl carbonate, 0.14 g K$_2$CO$_3$, and 0.25 g KI in 3 m DMF from using the procedure described in Example 4 above.

$^1$H-NMR(CDCl$_3$) δ 0.88 (t, 3H), 1.26 (t, 3H), 1.67 (m, 2H), 2.52 (t,2H), 2.94 (q, 2H), 3.79 (s, 3H), 5.41 (s, 2H), 5.79 (s, 2H), 6.76 (m, 2H), 6.94 (m, 6H), 7.06 (m, 2H), 7.2–7.5 (m, 12H), 7.9 (m, 1H).

Part C: Preparation of Methoxycarbonyloxymethyl 4-ethyl-2-propyl-1-[[2'-(tetrazol-5-yl)biphenyl-4-yl[methyl]imidazole-5-carboxylate 0.21 g of the title compound was obtained after chromatography (0% to 10% MeOH/CHC13 gradient) from 0.35 g methoxycarbonyloxymethyl 4-ethyl-2-propyl-1-[[2'-(N-triphenylmethyl(tetrazol-5-yl))biphenyl-4-yl]methyl]imidazole-5-carboxylate and 3 drops of 6 N HCl in 10 mL MeOH using the procedure described in Example 1 above.

$^1$H-NMR(CDCl$_3$) δ 0.83 (2t, 6H), 1.55 (m, 2H), 2.18 (t, 2H), 2.45 (q, 2H), 3.75 (s, 3H), 5.4 (s, 2H), 5.78 (s, 2H), 6.75 (m, 2H), 7.03 (m, 2H), 7.43–7.65 (m, 3H), 7.78 (m, 1H).

EXAMPLE 8

Methoxydimethylacetoxymethyl 4-ethyl-2-propyl-1-[[2'-(tetrazol-5-yl)biphenyl-4-yl]methyl]imidazole-5-carboxylate The title compound can be obtained using the procedure described in Example 4 above using chloromethyl methoxydimethylacetate.

EXAMPLE 9

Preparation of t-Butoxycarbonyloxymethyl 4-ethyl-2-propyl-1-[[2'-(tetrazol-5-yl)biphenyl-4-yl]methyl]imidazole-5-carboxylate Part A: Preparation of t-Butyl Chloromethyl Carbonate 0.62 mL pyridine was added dropwise to a solution of 0.77 g chloromethyl chloroformate and 1.32 mL t-BuOH in 60 mL CH$_2$Cl$_2$ cooled in an ice bath under an Ar atmosphere. The reaction was stirred 2 hours at 0° C. then transferred to a separatory funnel. The reaction was washed twice with H$_2$O, once with 10% CuSO$_4$, once with brine and dried with MgSO$_4$. Suction filtration and evaporation provided 0.55 g of desired product which was used without purification.

$^1$H-NMR(CDCl$_3$) δ 1.48 (s, 9H), 5.65 (s, 2H).

Part B: Preparation of t-Butoxycarbonyloxymethyl 4-ethyl-2-propyl-1-[[2'-(N-triphenylmethyl(tetrazol-5-yl))biphenyl-4-yl]methyl]imidazole-5-carboxylate 0.22 mL Et3N was added to a mixture of 0.700 g 4-ethyl-2-propyl-1-[[2'-(N-triphenylmethyl(tetrazol-5-yl))biphenyl-4-yl]methyl]imidazole-5-carboxylate, 0.26 g t-butyl chloromethyl carbonate and 0.59 g n-Bu$_4$NI in 5 mL dry THF under Ar. The reaction was stirred 6 days at room temperature and then concentrated on a rotary evaporator. The residue was partitioned between H$_2$O and CH$_2$Cl$_2$, and the organic extracts dried with MgSO$_4$. Flash chromatography using 1:1 EtOAc/petroleum ether(bp 40°-60° C.) gave 0.40 g of the title compound.

$^1$H-NMR(CDCl$_3$) δ 0.88 (t, 3H), 1.05 (t, 3H), 1.68 (m, 2H), 2.5 (t, 3H), 2.93 (q, 2H), 5.43 (s, 2H), 5.75 (s, 2H), 6.78 (m, 2H), 6.93 (m, 6H), 7.08 (m, 2H), 7.2-7.53 (m, 2H), 7.90 (m, 1H).

Part C: Preparation of t-Butoxycarbonyloxymethyl 4-ethyl-2-propyl-1-[[2'-(tetrazol-5-yl)biphenyl-4-yl]methyl]imidazole-5-carboxylate 0.43 g of the title compound was obtained after chromatography (0% to 10% MeOH/CHC13 gradient) from 0.40 g t-Butoxycarbonyloxymethyl 4-ethyl-2-propyl-1-[[2'-(N-triphenylmethyl(tetrazol-5-yl))biphenyl-4-yl]methyl]imidazole-5-carboxylate and 3 drops 6 N HCl in 10 mL MeOH using the procedure described in Example 1 above.

$^1$H-NMR(CDCl$_3$) δ 0.83 (m, 6H), 1.44 (s, 9H), 1.57 (m, 2H), 2.17 (m, 2H), 2.41 (m, 2H), 5.41 (s, 2H), 5.73 (s, 2H), 6.72 (m, 2H), 7.04 (m, 2H), 7.43 (m, 1H), 7.57 (m, 2H), 7.82 (m, 1H).

EXAMPLE 10

Preparation of 1-Acetoxyethyl 4-ethyl-2-propyl-1-[[2'-(tetrazol-5-yl)biphenyl-4-yl]methyl]imidazole-5-carboxylate Part A: Preparation of 1-Chloroethyl acetate 0.25 g of zinc chloride was added to a mixture of 3.6 g of acetaldehyde dimethyl acetal and 3 g of acetyl chloride. The mixture was warmed to 50° C. for 4 hours then cooled. The reaction mixture was quenched with ice-cold NaHCO$_3$, extracted with CH$_2$Cl$_2$, dried with Na$_2$SO$_4$ and the solvent evaporated to give the crude acetate which was used without further purification. MS (CH$_4$-CI) m/z 123.0 (M+H)$^+$.

Part B: Preparation of 1-Acetoxyethyl 4-ethyl-2-propyl-1-[[2'-(tetrazol-5-yl)biphenyl-4-yl]methyl]imidazole-5-carboxylate The title compound was obtained following the procedure described in Example 4 above using chloroethyl acetate.

$^1$H-NMR(CDCl$_3$) δ 0.91 (t, 3H), 1.21 (t, 3H), 1.71 (m, 2H), 1 75 (d, 3H), 2.05 (s, 3H), 2.6 (m, 2H), 2.75 (q, 2H), 5.41 (s, 2H), 6.85 (q, 1H), 6.92 (d, 2H), 7.08 (d, 2H), 7.2-7.35 (m, 3H), 7.8 (m, 1H).

EXAMPLE 11

Preparation of 1-(Methoxycarbonyl)ethyl 4-ethyl-2-propyl-1-[[2'-(tetrazol-5-yl)biphenyl-4-yl]methyl]imidazole-5-carboxylate Part A: Preparation of 1-Chloroethyl chloroformate 108 g of ethyl chloroformate was dissolved in 190 mL of sulfuryl chloride and then 0.24 g benzoyl peroxide was added. The mixture was refluxed for 5 hours and then cooled slightly. Excess sulfuryl chloride was distilled, then the product mixture was distilled through a 1 m spinning band column, 65° C. at 22 torr, to give 96 g of the product.

$^1$H-NMR(CDCl$_3$) δ 1.88 (d, 3H), 6.43 (q, 2H).

Part B: 1-Chloroethyl methyl carbonate 11.07 g of chloroethyl chloroformate, 5.8 g of methanol and 7.84 g of pyridine were added to 100 mL CH$_2$Cl$_2$ at 0° C. The reaction was stirred for one hour then the reaction mixture was quenched with water and acidified with IN HCl to pH 3. The mixture was then extracted with CH$_2$Cl$_2$, dried with Na$_2$SO$_4$ and the solvent evaporated to give the crude carbonate (12 g) which was used without further purification. $^1$H-NMR(CDCl$_3$) δ 1.83 (d, 3H), 3.84 (s, 3H), 6.42 (q, 2H).

Part C: Preparation 1-(Methoxycarbonyl)ethyl 4-ethyl-2-propyl-1-[[2'-(tetrazol-5-yl)biphenyl-4-yl]methyl]imidazole-5-carboxylate The title compound was obtained following the procedure described in Example 4 above using chloroethyl methyl carbonate. $^1$H-NMR(CDCl$_3$) δ 0.95 (m, 6H), 1.49 (d, 3H), 1.6 (m, 2H), 2.28 (m, 2H), 2.57 (q, 2H), 3.8 (s, 3H), 5.41 (dd, 2H), 6.77 (d, 2H), 6.82 (q, 1H), 7.05 (d, 2H), 7.42 (m, 1H), 7.57 (m, 2H), 7.84 (m, 1H).

EXAMPLE 12

Preparation of 1-(t-Butoxycarbonyl)ethyl 4-ethyl-2-propyl-1-[[2'-(tetrazol-5-yl)biphenyl-4-yl]methyl]imidazole-5-carboxylate Part A: Preparation of 1-Chloroethyl t-butyl carbonate 12 g of chloroethyl chloroformate, 14.55 g of t-butanol and 8.5 g of pyridine were added to 100 mL CH$_2$Cl$_2$ at 0° C. The reaction was stirred for one hour then the reaction mixture was quenched with water and acidified with 1N HCl to pH 3. The mixture was then extracted with CH$_2$Cl$_2$, dried with Na$_2$SO$_4$ and the solvent evaporated to give the crude carbonate (13.04 g) which was used without further purification.

$^1$H-NMR(CDCl$_3$) δ 1.53 (s, 9H), 1.83 (d, 3H), 6.39 (q, 2H).

Part B: Preparation of 1-(t-Butoxycarbonyl)ethyl 4-ethyl-2-propyl-1-[[2'-(tetrazol-5-yl)biphenyl-4-yl]methyl]imidazole-5-carboxylate The title compound was obtained following the procedure outlined in Example 4 using chloroethyl t-butyl carbonate.

$^1$H-NMR(CDCl$_3$) δ 0.92 (t, 3H), 1.14 (t, 3H), 1.14 (s, 9H), 1.51 (d, 3H), 1.62 (m, 2H), 2.47 (m, 2H), 2.92 (q, 2H), 5.4 (dd, 2H), 6.9 (d, 2H), 7.03 (d, 2H), 7.32 (m, 2H), 7.43 (m, 1H), 7.87 (m, 1H).

EXAMPLE 13

Preparation of 1,3-Dioxa-5-methyl-cyclopenten-2-one-4-ylmethyl 4-ethyl-2-propyl-1-[[2'-(tetrazol-5-yl)biphenyl-4-yl]methyl]imidazole-5-carboxylate Part A: (1,3-Dioxa-5-methyl-cyclopenten-2-one-4-yl)methyl 4-ethyl-2-propyl-1-[[2'-(N-triphenylmethyl(tetrazol-5-yl))biphenyl-4-yl]methyl]imidazole-5-carboxylate A mixture of 0.659 g 4-ethyl-2-propyl-1-[[2'-(N- triphenylmethyl(tetrazol-5-yl))biphenyl-4-yl]methyl]imidazole-5-carboxylic acid, 0.288 g 4- bromomethyl-1,3-dioxa-5-methyl-cyclopenten-2-one (*Chem. Pharm. Bull.* 32(6) 2241 (1984)), and 0.138 g K$_2$CO$_3$ in 3 mL dimethylformamide was stirred at room temperature under N$_2$ for 4 hours. The reaction was partitioned between 8 mL H$_2$O and 40 mL ethyl acetate. The organic extract was washed with H$_2$O (6×10 mL) and brine and dried with MgSO$_4$. Filtration, evaporation, and flash chromatography of the residue with a 0% to 5% MeOH/CHCl₃ gradient provided 0.75 g of the title compound.

¹H-NMR(CDCl₃) δ 0.88 (t, 3H, J=7.1 Hz), 1.14 (t, 3H, J=7.3 Hz), 1.67 (m, 2H), 2.06 (s, 3H), 2.52 (t, 2H, J=7.7 Hz), 2.91 (q, 2H, J=7.5 Hz), 4.81 (s, 2H), 5.55 (s, 2H), 6.73 (m, 2H), 6.95 (m, 6H), 7.07 (m, 2H), 7.22–7.39 (m, 10H), 7.45 (m, 2H), 7.86 (m, 1H).

Part B:
(1,3-Dioxa-5-methyl-cyclopenten-2-one-4-yl)methyl 4-ethyl-2-propyl-1-[[2'-(tetrazol-5-yl)biphenyl-4-yl]methyl]imidazole-5-carboxylate 4 drops 6 N HCl was added to a solution of 0.75 g of the above product in 10.5 mL MeOH in a N₂ atmosphere. The mixture was stirred at room temperature 2 days. The volatiles were evaporated and the residue immediately chromatographed using a 0% to 6% MeOH/CHCl₃ gradient. There was obtained 0.35 g of the desired compound as a white foam.

¹H-NMR(CDCl₃) δ 0.80–0.93 (m, 6H), 1.50–1.62 (m, 2H), 2.05 (s, 3H), 2.18–2.20 (t, 2H), 2.40–2.55 (q, 2H), 4.83 (s, 2H), 5.40 (s, 2H), 6.65–6.75 (d, 2H), 7.00–7.11 (d, 2H), 7.43–7.50 (m, 1H), 7.50–7.65 (m, 2H), 7.80–7.83 (m, 1H).

EXAMPLE 14

Preparation of
(5-1,1-Dimethylethyl)-1,3-dioxa-cyclopenten-2-one-4-yl(methyl 4-ethyl-2-propyl-1-[[2'-(tetrazol-5-yl)biphenyl-4-yl]methyl]imidazole-5-carboxylate Part A: Preparation of
2.2-Dimethyl-4-hydroxy-3-pentanone This compound was prepared from 2,2-dimethyl-3-pentanone *J. Chem. Soc.* 71, 4141 (1949); *J. Am. Chem. Soc.* 81, 2779 (1959)) by the general literature procedure (*Org. Synth.* 64, 118 (1985)).

0.24 g of cuprous chloride was suspended in 100 mL diethyl ether and then 22.1 g of propionyl chloride was added. The reaction was heated to reflux and 88 mL of t-butyl magnesium chloride was added slowly to maintain reflux. The reaction was stirred overnight then poured into 200 g ice and the pH adjusted to 8 with solid NaHCO₃. The reaction was extracted with ether, washed with 10% aq. NaHCO₃, water and then brine followed by MgSO₄ drying. The product was purified by distillation to give 12.5 g of the ketone.

¹H-NMR(CDCl₃) δ 1.15 (s, 9H), 1.27 (d, 3H), 3.40 (br d, 1H), 4.56 (m, 1H).

Part B:
4-Bromomethyl-5-(1.1-dimethylethyl)-1.3-dioxacyclopenten-2-one

This material was prepared from 2,2-dimethyl-4-hydroxy-3-pentanone by the literature procedure described in (*Chem. Pharm. Bull.* 32, 2241 (1984)).

1.94 g of 2,2-dimethyl-4-hydroxy-3-pentanone was dissolved in 15 mL of benzene and cooled to 0° C. 23 mL of phosgene in toluene was added followed by 23 mL pyridine and 20 mL toluene. The reaction was stirred overnight, the solids filtered and the filtrate washed with 10% HCl then water and then dried with MgSO₄. Crude material was dissolved in 15 mL xylenes then 0.4 g p-TsOH was added and the reaction heated to reflux. The reaction was quenched with saturated aq. NaHCO₃ then distilled at 100°–125° C. at 1 torr.

¹H-NMR(CDCl₃) δ 1.31 (s, 9H), 4.28 (s, 2H).

Part C: Preparation of
(5-(1,1-Dimethylethyl)-1,3-dioxa-cyclopenten-2-one-4-yl)methyl 4-ethyl-2-propyl-1-[[2'-(N-triphenyl methyl(tetrazol-5-yl))biphenol-4-yl[methyl[imidazole-5-carboxylate 0.620 g of the title compound was obtained from 0.32 g 4-bromomethyl-5-(1,1-dimethylethyl)-1,3-dioxacyclopenten-2-one and 0.60 g 4-ethyl-2-propyl-1-[[2'-(N-triphenylmethyl(tetrazol-5-yl))biphenyl-4yl]methyl]imidazole-5-carboxylic acid using the method shown in Example 13 above.

¹H-NMR(CDCl₃) δ 0.86 (t, 3H), 1.23 (t, 3H), 1.25 (s, 9H), 1.70 (m, 2H), 2.49 (t, 2H), 2.90 (q, 2H), 4.99 (s, 2H), 5.40 (s, 2H), 6.75 (m, 1H), 6.95 (m, 6H), 7.08 (m, 2H), 7.2–7.5 (m, 12H), 7.88 (m, 1H).

Part D: Preparation of
(5-(1.1-Dimethylethyl)-1.3-dioxa-cyclopenten-2-one-4-yl)methyl 4-ethyl-2-propyl-1-[[2'-(tetrazol-5-yl)biphenyl-4-yl)methyl]imidazole-5-carboxylate 0.40 g of the title compound was obtained from 0.62 g (5-(1,1-dimethylethyl)-1,3-dioxa-cyclopenten-2-one-4-yl)methyl 4-ethyl-2-propyl-1-[[2'-(N-triphenylmethyl(-tetrazol-5-yl))bihenyl-4-yl]methyl]imidazole-5-carboxylate using the method shown in Example 13 above.

¹H-NMR(CDCl₃) δ 0.85 (t, 3H), 0.93 (t, 3H), 1.26 (s, 9H), 1.60 (m, 2H), 2.25 (t, 2H), 2.56 (q, 2H), 5.01 (s, 2H), 5.41 (s, 2H), 6.77 (m, 2H), 7.08 (m, 2H), 7.42 (m, 1H), 7.59 (m, 2H), 7.88 (m, 1H).

EXAMPLE 15

Preparation of
(1,3-dioxa-5-phenyl-cyclopenten-2-one-4-yl)methyl 4-ethyl-2-propyl-1-[[2'-(tetrazol-5-yl)biphenyl-4-yl[methyl[imidazole-5-carboxylate Part A: Preparation of 2-Hydroxy-propiophenone This was prepared from propiophenone by the general literature procedure described in *Org. Synth.* 64, 118 (1985).

6 g of the TMS ether of propiophenone was dissolved in 225 mL hexane and cooled to −15° C. 9.2 g MCPBA was added and the reaction stirred for 20 minutes at −15° C. then room temperature for 2 hours. The reaction was filtered then evaporated to give an oil which was diluted with 150 mL ethyl acetate, washed with 1.5N HCl and stirred for 20 minutes. This was neutralized with NaHCO₃ then extracted with ethyl acetate then washed with brine. The product was purified by chromatography to give 2.52 g product.

¹H-NMR(CDCl₃) δ 1.46 (d, 3H), 3.83 (d, 1H) 5.17 (m, 1H), 7.51 (m, 2H), 7.63 (m, 1H), 7.92 (m, 2H).

Part B:
1.3-Dioxa-4-methyl-5-phenyl-cyclopenten-2-one

This compound was prepared from 2-hydroxypropiophenone by the literature procedure described in *Liebigs Ann. Chem.* 764, 116 (1972).

The hydroxyketone was dissolved in CH₂Cl₂ at 0° C. and 26 mL phosgene in toluene was added followed by 3 g dimethylaniline. Stirred overnight at room temperature. Washed with 10% HCl, water and brine then dried with MgSO₄. Distillation (100° C. at 0.06 torr) gave 2.74 g of product.

¹H-NMR(CDCl₃) δ 2.39 (s, 3H), 7.35–7.50 (m, 5H).

Part C: 4-Bromomethyl-1,3-dioxa-5-phenyl-cyclopenten-2-one

This compound was prepared from 1,3-dioxa-4-methyl-5-phenyl-cyclopenten-2-one by the literature procedure described in *Chem. Pharm. Bull.* 32, 2241 (1984).

2.74 g of 1,3-dioxa-4-methyl-5-phenyl-cyclopenten-2-one, 3.32 g NBS and 0.0613 g AIBN were refluxed overnight. The reaction was cooled to 0° C. then filtered. The filtrate was evaporated then recrystallized from benzene/cyclohexane to give 1.5 g of product.

$^1$H-NMR(CDCl$_3$) δ 4.45 (s, 2H), 7.55 (m, 5H).

Part D: (1.3-Dioxa-5-phenyl-cyclopenten-2-one-4-yl)methyl 4-ethyl-2-propyl-1-2'-(N-triphenylmethyl(tetrazol-5-yl))biphenyl-4-yl]methyl]imidazole-5-carboxylate 0.220 g of the title compound were obtained from 0.3826 g 4-bromomethyl-1,3-dioxa-5-phenyl-cyclopenten-2-one and 0.6588 g 4-ethyl-2-propyl-1-[[2'-(N-triphenylmethyl(tetrazol-5-yl))biphenyl-4yl]methyl-]imidazole-5-carboxylic acid using the procedure described in Example 1 above.

Part E: Preparation of (1,3-Dioxa-5-phenyl-cyclopenten-2-one-4-yl)methyl 4-ethyl-2-propyl-1-[[2'-(tetrazol-5-yl)biphenyl-4-yl[methyl]imidazole-5-carboxylate 0.15 of the title compound was obtained from 0.22 g (1,3-dioxa-5-phenyl-cyclopenten-2-one-4-yl)methyl 4-ethyl-2-propyl-1-[[2'-(N-triphenylmethyl(tetrazol-5-yl))biphenyl-4-yl]methyl]imidazole-5-carboxylate using the procedure described in Example 1 above.

R$_f$(silica gel, MeOH/CHCl$_3$ 1:9) 0.45.

The compounds described in Examples 1-15 above are set forth in Table 1.

TABLE 1

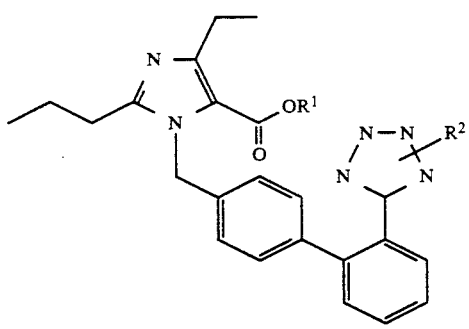

| Example | R$^1$ | R$^2$ | physical data |
|---|---|---|---|
| 1 | propyl | H | NMR |
| 2 | CH$_2$N(CH$_3$)$_2$ | H | NMR |
| 3 | CH$_2$O$_2$CCH$_3$ | H | NMR |
| 4 | CH$_2$O$_2$CCH(CH$_3$)$_2$ | H | NMR |
| 5 | CH$_2$O$_2$CC(CH$_3$)$_3$ | H | NMR |
| 6 | CH$_2$O$_2$CC(CH$_3$)$_3$ | CH$_2$O$_2$CC(CH$_3$)$_3$ | NMR |
| 7 | CH$_2$O$_2$COCH$_3$ | H | NMR |
| 8 | CH$_2$O$_2$COC(OCH$_3$)(CH$_3$)$_2$ | H | NMR |
| 9 | CH$_2$O$_2$COC(CH$_3$)$_3$ | H | NMR |
| 10 | CH(CH$_3$)O$_2$CCH$_3$ | H | NMR |
| 11 | CH(CH$_3$)O$_2$COCH$_3$ | H | NMR |
| 12 | CH(CH$_3$)O$_2$COC(CH$_3$)$_3$ | H | NMR |

TABLE 1-continued

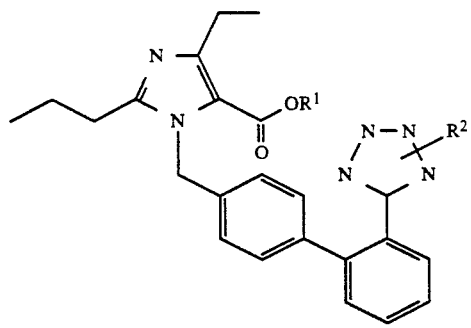

| Example | R$^1$ | R$^2$ | physical data |
|---|---|---|---|
| 13 | ![structure with O-C(=O)-O-C(CH3)=] | H | NMR |
| 14 | ![structure with O-C(=O)-O-C(C(CH3)3)=] | H | NMR |
| 15 | ![structure with O-C(=O)-O-C(Ph)=] | H | TLC |

Additional examples are shown in Table 2 which can be made according to the procedures outlined above.

TABLE 2

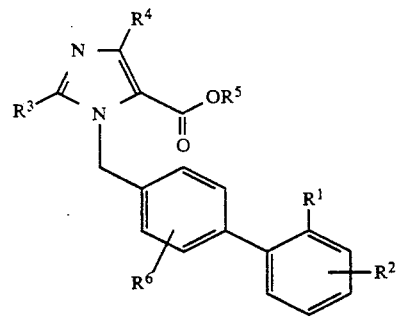

| Example | R$^1$ | R$^2$ | R$^3$ | R$^4$ | R$^5$ | R$^6$ |
|---|---|---|---|---|---|---|
| 16 | Tet | H | Et | Et | CH$_2$O$_2$CC(CH$_3$)$_3$ | H |
| 17 | Tet | H | n-Pr | Et | CH$_2$O$_2$CC(CH$_3$)$_3$ | H |
| 18 | Tet | H | n-Bu | Et | CH$_2$O$_2$CC(CH$_3$)$_3$ | H |
| 19 | Tet | H | n-Pr | Et | CH$_2$O$_2$CC(CH$_3$)$_3$ | F |
| 20 | Tet | H | n-Pr | C$_2$F$_5$ | CH$_2$O$_2$CC(CH$_3$)$_3$ | F |
| 21 | Tet | Et | n-Pr | Cl | CH$_2$O$_2$COC(CH$_3$)$_3$ | H |
| 22 | Tet | n-Pr | n-Bu | Cl | CH$_2$O$_2$COC(CH$_3$)$_3$ | H |
| 23 | Tet | OEt | n-Pr | Cl | CH$_2$O$_2$COC(OCH$_3$)(CH$_3$)$_2$ | H |
| 24 | Tet | H | n-Bu | n-Pr | CH$_2$O$_2$COCH(CH$_3$)$_2$ | Me |
| 25 | Tet | H | n-Bu | n-Pr | CH$_2$O$_2$COCH(CH$_3$)$_2$ | Me |

Tet = Tetrazole

UTILITY

Angiotensin-II (AII) produces numerous biological responses (e.g. vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by [Chiu, et al., Receptor, 1 33, (1990)]. In brief, aliquots of a freshly prepared particulate fraction of rat adrenal cortex were incubated with 0.05 nM [$^{125}$I]AII and varying concentrations of potential AII antagonists in a Tris buffer. After a 1 h incubation the reaction was terminated by addition of cold assay buffer. The bound and free radioactivity were rapidly separated through glass-fiber filters, and the trapped radioactivity was quantitated by scintillation counting. The inhibitory concentration ($IC_{50}$) of potential AII antagonists which gives 50% displacement of the total specifically bound [$^{125}$I]AII is presented as a measure of the affinity of such compound for the AII receptor.

Using the assay method described above, the compounds of this invention are found to exhibit an activity of at least $IC_{50} < 10$ micromolar, thereby demonstrating and confirming the activity of these compounds as effective AII antagonists. Results are presented in Table 3.

TABLE 3

| Example | Angiotensin II Receptor Binding $IC_{50}$ nM |
| --- | --- |
| 2 | 100 |
| 5 | 2 |
| 6 | 20 |
| 7 | 3 |
| 9 | 6 |
| 10 | 20 |
| 11 | 4 |
| 12 | 5 |
| 13 | 3 |
| 14 | 3 |
| 15 | 6 |

The potential antihypertensive effects of the compounds of this invention may be demonstrated by administering the compounds to awake rats made hypertensive by ligation of the left renal artery [Cangiano, et al., J. Pharmacol. Exp. Ther., 1979, 208, 310]. This procedure increases blood pressure by increasing renin production with consequent elevation of AII levels. Compounds are administered intravenously via cannula in the jugular vein to give a cumulative dose of 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds.

Using the in vivo methodology described above, the compounds of this invention are found to exhibit an activity (intravenous) which is 10 mg/kg or less, and/or an activity (oral) which is 100 mg/kg or less, thereby demonstrating and confirming the utility of these compounds as effective agents in lowering blood pressure. The results are described in Table 4.

TABLE 4

| Examples | Oral Antihypertensive Effects in Renal Hypertensive Rats $ED_{30}$ mg/kg |
| --- | --- |
| 5 | 0.03 |
| 8 | 0.03 |
| 9 | 0.02 |
| 11 | 0.02 |
| 12 | 0.3 |
| 13 | 0.1 |
| 14 | 0.3 |
| 15 | 0.3 |

The compounds of the invention can be administered for the treatment of hypertension by any means that effects contact of the active ingredient compound with the site of action in the body of a warm-blooded animal. For example, administration can be parenteral, i.e., subcutaneous, intravenous, intramuscular, or intraperitoneal. Preferably, administration is by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice. The compounds of the invention are useful in treating hypertension. They are also of value in the management of acute and chronic congestive heart failure and angina. These compounds may also be expected to be useful in the treatment of primary and secondary hyperaldosteronism; renal diseases such as diabetic nephropathy, glomerulonephritis, glomerular sclerosis, nephrotic syndrome, hypertensive nephrosclerosis, end stage renal disease, used in renal transplant therapy, and to treat renovascular hypertension, scleroderma, left ventricular dysfunction, systolic and diastolic dysfunction, diabetic retinopathy and in the management of vascular disorders such as migrane, Raynaud's disease, and as prophylaxis to minimize the atherosclerotic process and neointimal hyperplasia following angioplasty or vascular injury and to retard the onset of type II diabetes. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels and the like. Pharmaceutical formulations prepared to treat intraocular pressure would typically containing about 0.1% to 15% by weight, preferably 0.5% to 2% by weight, of a compound of this invention. For this use, the compounds of this invention may also be used in combination with other medications for the treatment of glaucoma including choline esterase inhibitors such as physostigmine salicylate or demecarium bromide, parasympathomimetic agents such as pilocarpine nitrate, $\beta$-adrenergic antagonists such as timolol maleate, adrenergic agonists such as epinephrine and carbonic anhydrase inhibitors such as MK-507.

The term, "a warm-blooded animal" as used herein means a member of the animal kingdom possessed of a homeostatic mechanism and includes mammals and birds.

In the management of hypertension and the clinical conditions noted above, the compounds of this invention may be utilized with a pharmaceutical carrier in compositions such as tablets, capsules or elixirs for oral administration, suppositories for rectal administration, sterile solutions or suspensions for parenteral or intramuscular administration, and the like. The compounds of this invention can be administered a warm-blood animal in need of such treatment in dosages that will provide optimal pharmaceutical efficacy. Although the dose will vary from patient to patient depending upon the nature and severity of disease, the patient's weight, special diets being followed by a patient, concurrent medication, and other factors which those skilled in the art will recognize, the dosage range will generally be about 1 to 1000 mg per patient per day which can be administered in single or multiple doses. Preferably, the dosage range will be about 5 to 500 mg per patient per day; more preferably about 5 to 300 mg per patient per day.

The compounds of this invention can also be administered in combination with other antihypertensives and/or diuretics. For example, the compounds of this invention can be given in combination with diuretics such as hydrochlorothiazide, chlorothiazide, chlorthalidone, methylclothiazide, furosemide, ethacrynic acid, triamterene, amiloride spironolactone and atriopeptin; calcium channel blockers, such as diltiazem, felodipine, nifedipine, amlodipine, nimodipine, isradipine, nitrendipine and verapamil; β-adrenergic antagonists such as timolol, atenolol, metoprolol, propanolol, nadolol and pindolol; angiotensin converting enzyme inhibitors such as enalapril, lisinopril, captopril, ramipril, quinapril and zofenopril; renin inhibitors such as A-69729, FK 906 and FK 744; α-adrenergic antagonists such as prazosin, doxazosin, and terazosin; sympatholytic agents such as methyldopa, clonidine and guanabenz; atriopeptidase inhibitors (alone or with ANP) such as UK-79300; serotonin antagonists such as ketanserin; $A_2$-adrenosine receptor agonists such as CGS 22492C; potassium channel agonists such as pinacidil and cromakalim; and various other antihypertensive drugs including reserpine, minoxidil, guanethidine, hydralazinc hydrochloride and sodium nitroprusside as well as combinations of the above-named drugs. Combinations useful in the management of congestive heart failure include, in addition, compounds of this invention with cardiac stimulants such dobutamine and xamoterol and phosphodiesterase inhibitors including amrinone and milrinone.

Typically, the individual daily dosages for these combinations can range from about one-fifth of the minimally recommended clinical dosages to the maximum recommended levels for the entities when they are given singly. To illustrate these combinations, one of the angiotensin-II antagonists of this invention effective clinically in the 5-500 milligrams per day range can be effectively combined at levels at the 1.0-500 milligrams per day range with the following compounds at the indicated per day dose range: hydrochlorothiazide (6-100 mg), chlorothiazide (1250-500 mg), furosemide (5-80 mg), propranolol (10-480 mg), timolol maleate (1-20 mg) methyldopa (125-2000 mg), felodipine (1-20 mg), nifedipine (5-120 mg), nitrendipine (5-60 mg), and diltiazem (30-540 mg). In addition, triple drug combinations of hydrochlorothiazide (5-100 mg) plus amiloride (5-20mg) plus angiotensin-II antagonists of this invention (1-500 mg) or hydrochlorothiazide (5-100 mg) plus timolol maleate (5-60 mg) plus an angiotensin-II antagonists of this invention (1-500 mg) or hydrochlorothiazide (5-200 m g) and nifedipine (5-60 mg) plus an angiotensin-II antagonists of this invention (1-500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

The active ingredient can be administered orally in solid dosage forms, such as capsules, tablets, and powders, or in liquid dosage forms, such as elixirs, syrups, and suspension. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated for film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol., a standard reference text in this field.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

What is claimed is:
1. A compound of the formula:

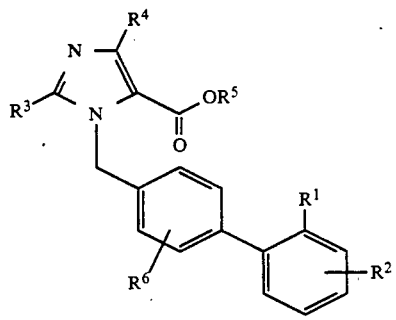   I wherein
$R^1$ is —$CO_2H$ or

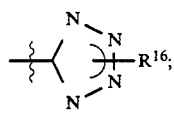

$R^2$ is
  (a) H,
  (b) C1–C5-alkyl,
  (c) C1–C5-alkoxy,
  (d) halo (F, Cl),
  (e) phenyl;
$R^3$ is C1–C5-alkyl, C2–C5-alkenyl, C2–C5-alkynyl;
$R^4$ is
  (a) H,
  (b) halo (Cl, Br, I),
  (c) C1–C6-alkyl,
  (d) $C_vF_w$ where v=1 to 3 and w=1 to (2v+1);
$R^5$ is
  (a) —$(CH_2)_pNR^{12}R^{13}$,
  (b) —$(CH_2)_sCH(R^7)(CH_2)_s$, $O_2CR^8$,
  (c)

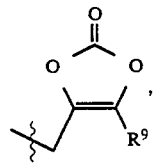

(d) —$(CH_2)_pCO_2R^{10}$,
  (e)

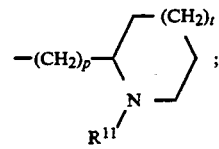

$R^6$ is
  (a) H,
  (b) halogen (F, Cl, Br, I),
  (c) C1–C5-alkyl,
  (d) —OH,
  (e) C1–C4-alkoxy,
  (f) —$NO_2$,
  (g) —$NR^{12}R^{13}$,
  (h) —$NR^{12}COR^{15}$,
  (i) —$NR^{12}CO_2R^{15}$,
  (j) —$S(O)_rR^{14}$ where r is 0, 1 or 2,
  (h) —$CO_2R^{15}$,
  (i) —$C_vF_w$ where v=1 to 3 and w=1 to (2v+1),
  (J) —$OC_vF_w$ where v=1 to 3 and w=1 to (2v+1),
  or (K) —CN;
$R^7$ is H or C1–C4-alkyl;
$R^8$ is
  (a) H,
  (b) C1–C5-alkyl,
  (c) C1–C5-alkyl optionally substituted with a group consisting of:
    i) C1–C5-alkoxy,
    ii) aryl, wherein aryl is phenyl or napthyl optionally substituted with one or two substituents selected from the group consisting of halo (F, Cl, Br, I), C1–C4-alkyl, C1–C4-alkoxy, —$NO_2$, —$S(O)_r$(C1–C5-alkyl), —OH, —$NR^{12}R^{13}$, —$CO_2R^{15}$, and —$C_vF_w$ where v=1 to 3 and w=1 to (2v+1);
$R^9$ is
  (a) C1–C5-alkyl,
  (b) —$C_vF_w$ where v=1 to 3 and w=1 to (2v+1),
  (c) C1–C5-alkyl optionally substituted with a group consisting of:
    i) C1–C5-alkoxy,
    ii) phenyl or phenyl substituted with at least one substituent selected from the group consisting of halo (F, Cl, Br, I), C1–C4-alkyl, C1–C4-alkoxy, —$NO_2$, —$S(O)_r$(C1–C4-alkyl), —OH, —$NR^{12}R^{13}$, —$CO_2R^{15}$, and —$C_vF_w$ where v=1 to 3 and w=1 to (2v+1),
    iii) benzyl or benzyl substituted with at least one substituent selected from the group consisting of halo (F, Cl, Br, I), C1–C4-alkyl C1–C4-alkoxy, —$NO_2$, —$S(O)_r$(C1–C4-alkyl), —OH, —$NR^{12}R^{13}$, —$CO_2R^{15}$, and —$C_vF_w$ where v=1 to 3 and w=1 to (2v+1);
$R^{10}$ is (a) phenyl or phenyl substituted with at least one substituent selected from the group consisting of halo (F, Cl, Br, I), C1-C4-alkyl C1-C4-alkoxy, —NO₂, —S(O)ᵣ(C1-C4-alkyl), —OH-, —NR¹²R¹³, —CO₂R¹⁵, and —CᵥFw where v=1 to 3 and w=1 to (2v+1);

(b) benzyl or benzyl substituted with at least one substituent selected from the group consisting of halo (F, Cl, Br, I), C1-C4-alkyl C1-C4-alkoxy, —NO₂, —S(O)ᵣ(C1-C4-alkyl), —OH-, —NR¹²R¹³, —CO₂R¹⁵, and —CᵥFw where v=1 to 3 and w=1 to (2v+1);

R¹¹ is H, C1-C5-alkyl or benzyl;
R¹² and R¹³ are independently H, C1-C5-alkyl, phenyl or benzyl;
R¹⁴ is CF₃, C1-C5-alkyl, or phenyl;
R¹⁵ is H, C1-C5-alkyl, or NR¹²R¹³;
R¹⁶ is H or CH₂O₂CC(CH₃)₃;
p is 1-5;
r is 0-2;
s and s' are 0-5;
t is 0 or 1;
or a pharmaceutically acceptable salt thereof.

2. A compound according to claim 1 wherein
R¹ is

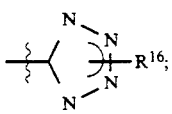

R² is H;
R³ is C1-C5-alkyl;
R⁵ is
(a) —(CH₂)ₛCH(R⁷)(CH₂)ₛ, O₂CR⁸
(b)

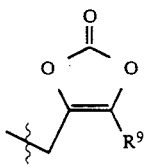

R⁶ is H;
R⁷ is H;
R⁸ is
(a) H,
(b) C1-C5-alkyl,
(c) C1-C5-alkoxy,
(d) C1-C5,-alkyl optionally substituted with a group consisting of:
  i) C1-C5-alkoxy;
R⁹ is
(a) C1-C5-alkyl,
(b) C1-C5-alkyl optionally substituted with a group consisting of:

i) C1-C5-alkoxy,
ii) phenyl or phenyl substituted with at least one substituent selected from the group consisting of halo (F, Cl, Br, I), alkyl, C1-C5-alkoxy, —OH;
iii) benzyl or benzyl substituted with at least one substituent selected from the group consisting of halo (F, Cl, Br, I), C1-C5-alkoxy, —OH;

p is 1;
s is 1;
s' is 0.

3. A compound according to claim 1 wherein
R¹ is

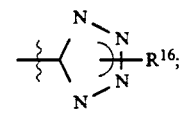

R² is H;
R³ is C1-C5-alkyl;
R⁵ is —(CH₂)ₛCH(R⁷)(CH₂)ₛO₂CR⁸;
R⁷ is H;
R⁸ is
(a) C1-C5-alkoxy,
(b) C1-C5-alkyl,
(c) C1-C5-alkyl optionally substituted with a group consisting of:
  i) C1-C5-alkoxy;
p is 1;
s is 1;
s' is 0.

4. A compound according to claim 1 which is trimethylacetoxymethyl 4-ethyl-2-propyl-1-[[2'-(tetrazol-5-yl)biphenyl-4-yl]methyl]imidazole-5-carboxylate.

5. A compound according to claim 1 which is methoxycarbonyloxymethyl 4-ethyl-2-propyl-1-[[2'-(tetrazol-5-yl)biphenyl-4-yl]methyl]imidazole-5-carboxylate.

6. A compound according to claim 1 which is t-butoxycarbonyloxymethyl 4-ethyl-2-propyl-1-[[2'-(tetrazol-5-yl)biphenyl-4-yl]methyl]imidazole-5-carboxylate.

7. A compound according to claim 1 which is 1-(Methoxycarbonyl)ethyl 4-ethyl-2-propyl-1-[[2'-(tetrazol-5-yl)biphenyl-4-yl]methyl]imidazole-5-carboxylate.

8. A pharmaceutical composition comprising a pharmaceutically suitable carrier and a therapeutically effective amount of the compound of any one of claims 1 through 7.

9. A method of treating hypertension in a warm-blooded animal comprising orally administering to the animal a therapeutically effective amount of a compound of any one of claims 1 through 7.

10. A method of treating congestive heart failure in a warm-blooded animal comprising orally administering to the animal a therapeutically effective amount of a compound of any one of claims 1 through 7.

* * * * *

UNITED STATES PATENT AND TRADEMARK OFFICE
CERTIFICATE OF CORRECTION

PATENT NO. : 5,310,929

DATED : May 10, 1994

INVENTOR(S) : Robert J. Ardecky, Carol L. Ensinger and James R. Pruitt

It is certified that error appears in the above-identified patent and that said Letters Patent is hereby corrected as shown below:

Column 32, line 38, delete "C1-C5-alkyl," and insert --C1-C5-alkoxy,--.

Column 33, line 52, delete "(b) C1-C5-alkyl,".

Column 33, line 53, delete "(c)" and insert --(b)--.

Column 33, line 54, delete "(d)" and insert --(c)--.

Column 34, line 27, delete "(b) C1-C5-alkyl,".

Column 34, line 28, delete (c) and insert --(b)--.

Signed and Sealed this

Seventeenth Day of September, 1996

*Attest:*

BRUCE LEHMAN

*Attesting Officer*  *Commissioner of Patents and Trademarks*